United States Patent [19]
Zwaal

[11] Patent Number: 6,122,053
[45] Date of Patent: Sep. 19, 2000

[54] APPARATUS FOR MEASURING PARTICLE FALLOUT ON A SURFACE USING A TELLTALE PLATE

[75] Inventor: Arie Zwaal, Katwijk aan Zee, Netherlands

[73] Assignee: Agence Spatiale Europeene, Paris, France

[21] Appl. No.: 09/051,415

[22] PCT Filed: Sep. 26, 1996

[86] PCT No.: PCT/FR96/01505

§ 371 Date: Apr. 7, 1998

§ 102(e) Date: Apr. 7, 1998

[87] PCT Pub. No.: WO97/14030

PCT Pub. Date: Apr. 17, 1997

[30] Foreign Application Priority Data

Oct. 9, 1995 [FR] France .................................. 95 11869

[51] Int. Cl.[7] ................................................ G01N 21/00
[52] U.S. Cl. ............................................ 356/338; 356/337
[58] Field of Search .................................... 356/337–340, 356/343, 237.1; 250/563, 572, 205, 701; 358/199, 200

[56] References Cited

U.S. PATENT DOCUMENTS 4,614,427  9/1986  Koizumi et al. ........................ 356/237

5,046,847  9/1991  Nakata et al. ........................... 356/338

FOREIGN PATENT DOCUMENTS 0 678 910 A2  10/1995  European Pat. Off. .
1145657  3/1969  United Kingdom .

Primary Examiner—Frank G. Font
Assistant Examiner—Michael P. Stafira
Attorney, Agent, or Firm—Sughrue, Mion, Zinn, Macpeak & Seas, PLLC

[57] ABSTRACT

An apparatus for measuring fallout of particles on a surface of the type using a telltale plate which is exposed for a particular time period to the fallout of the particles. The apparatus illuminates the telltale plate when it is inserted into the measuring apparatus with the illuminating structure being adapted to emit at least one light beam substantially parallel to the upper surface. An opto-electronic device ir, used to detect light diffused by the particles when illuminated and is adapted to measure the intensity of the light diffused in a direction orthogonal to the surface and to deduce therefrom the degree of contamination per unit surface of the telltale plate by the annular structure around the telltale plate and supporting an optical enclosure and the telltale plate illuminating structure comprises at least two monochromatic optical sources fixed to the annular structure and regularly spaced around the telltale plate to illuminate the upper surface of the telltale plate in the same number of separate directions and at a grazing incidence.

10 Claims, 2 Drawing Sheets

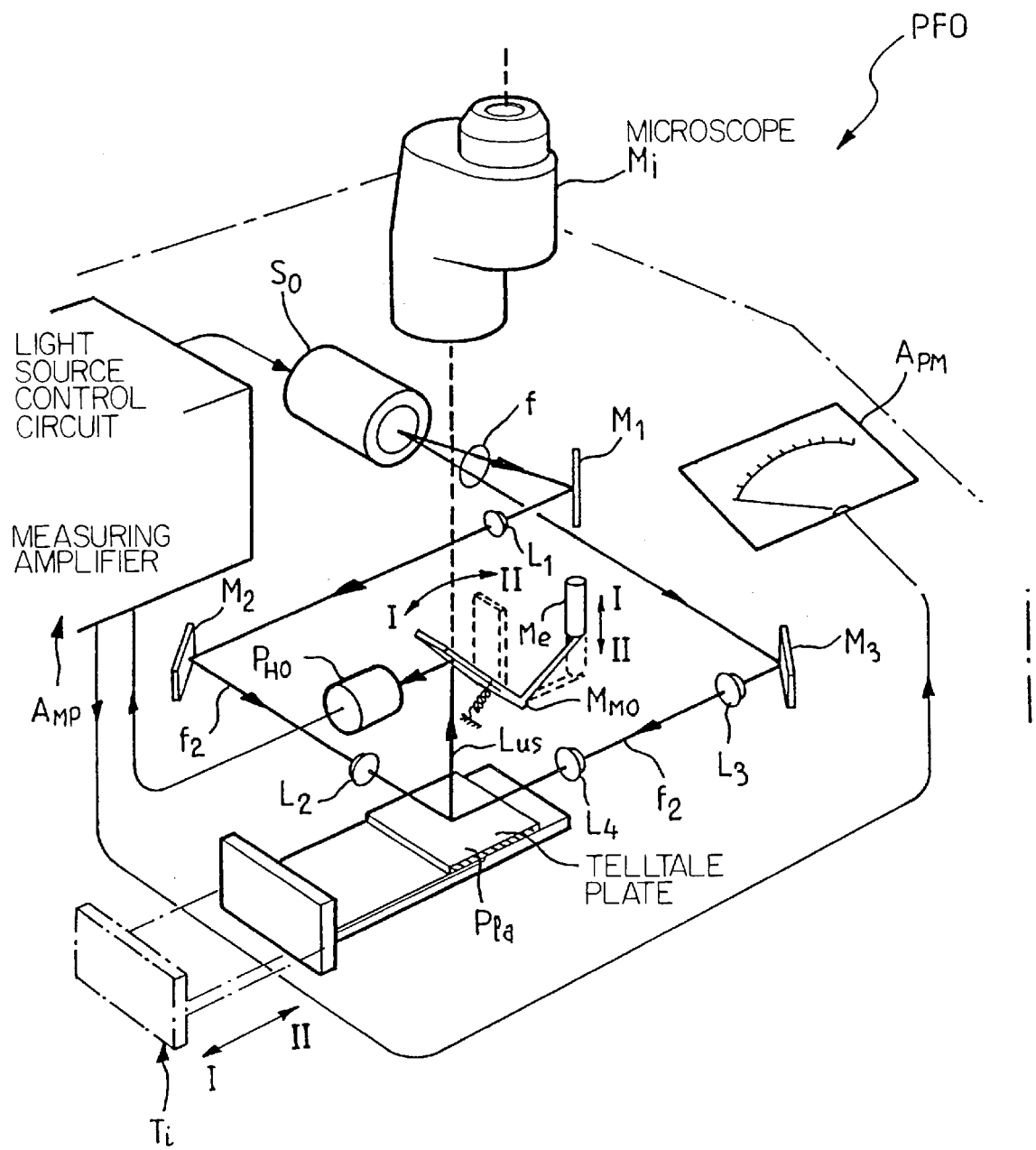
FIG_1
PRIOR ART

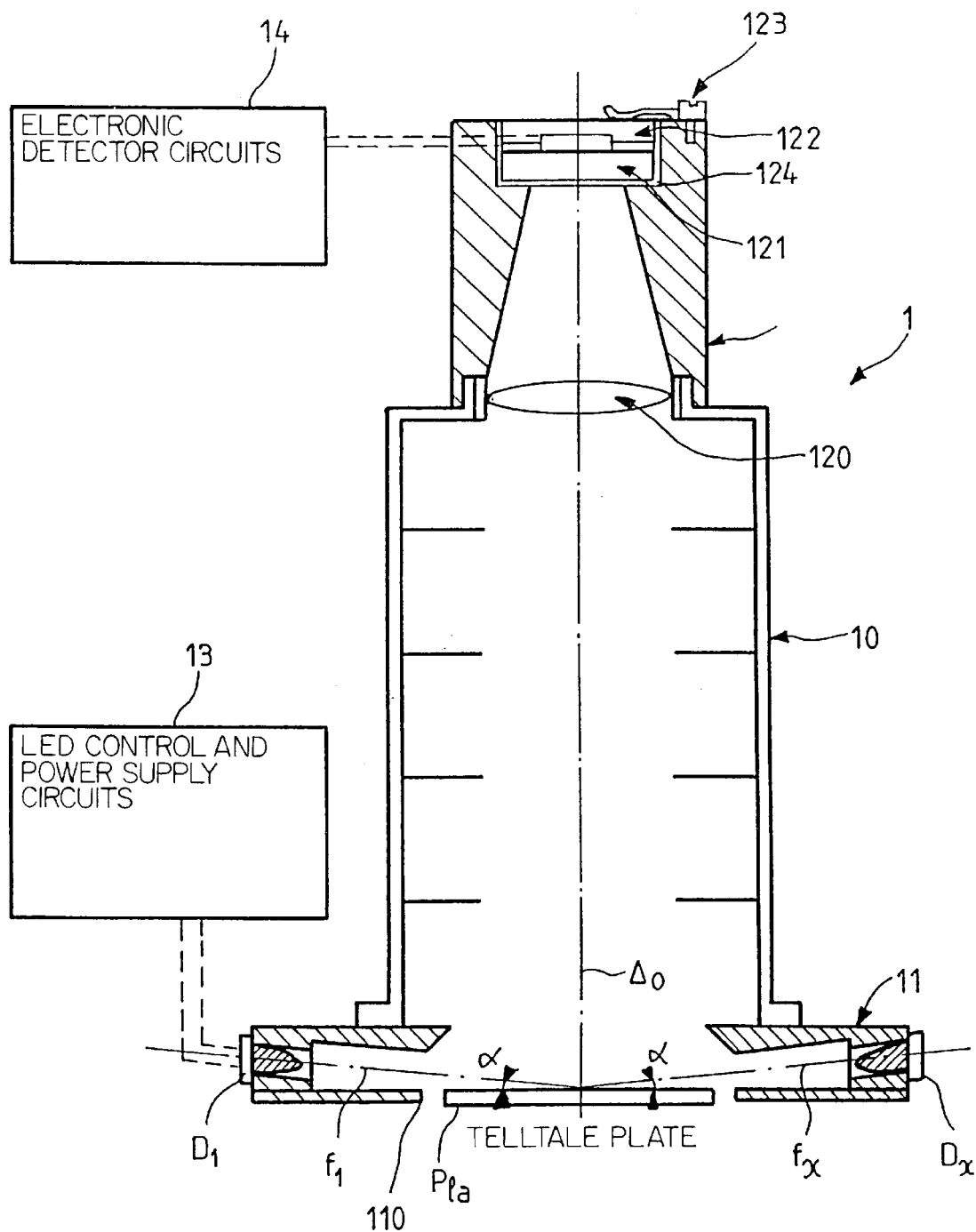

APPARATUS FOR MEASURING PARTICLE FALLOUT ON A SURFACE USING A TELLTALE PLATE

BACKGROUND OF THE INVENTION

1. Field of the Invention

The invention concerns an instrument for measuring particle fallout on a surface using a telltale plate.

2. Related Art

In many industries it is necessary to protect all kinds of products, objects, devices, etc from contamination, in particular by particles. This is the case in particular in the fabrication of integrated circuits, measuring instrumentation for aircraft or spacecraft, medical instrumentation, thin film devices, pharmaceutical preparations, photographic emulsions, etc. In all such applications the slightest contamination can reduce output or shorten service life. Monitoring contaminants that can be deposited on a product is therefore vital for this type of industry.

For this reason, production and inspection are carried out in "white rooms" and the air entering such rooms is filtered to minimize the risk of contamination. Additionally, the pressure is raised relative to the external surroundings. However, because of the activity of the personnel present, a large quantity of particles is emitted into the environment of such rooms. The effect of gravity on such particles causes them to settle on all surfaces of the room and, more importantly, on the products being fabricated or assembled.

Initially the contamination of products in "white rooms" was not measured directly. Instead of such direct measurement the size and the number of particles in suspension per unit volume were measured. However, this method could give only a highly uncertain indication of the exact degree of contamination of the products themselves due to the fallout of particles. The larger particles generated by a given operative tend to settle faster in the immediate vicinity of the operative in question. What is more, she operative is likely to move around inside the protected enclosure. Th above method had major drawbacks.

It has been proposed to measure the contamination of surfaces due to the fallout of particles using sampling surfaces in the form of telltale plates. These telltale plates are placed in the immediate vicinity of the product during fabrication or the device during assembly. Particles in suspension can therefore settle freely on the telltale plates for a specified time period. At the end of this specified time period the aforementioned plates are collected and the particle deposit is measured using optical apparatus based on a photometer.

The above method has a number of advantages. Firstly, the accuracy of the measurements is greatly enhanced: in particular it allows for the heaviest particles produced by the operatives, since the plates are disposed near them when they are working on a given product or device. It is simple to use and less costly than methods previously used. It can also measure the quality of the renewed air, for which purpose it is sufficient to carry out measurements during periods of inactivity.

Apparatus for carrying out measurements by the above method has been developed by SAAB AKTIEBOLAG and is described in British patent application GB-A-1 145 657.

FIG. 1 is a diagrammatic illustration of the operating principle of measuring apparatus of the above kind.

The telltale plate $P_{la}$ is contained in a plate-carrier (not shown) to prevent accidental contamination. During the measurement it is placed on a mobile drawer $T_i$ (position I: out of measuring apparatus, position II: measuring position). Once introduced into the measuring apparatus PFO the telltale plate $P_{la}$ is illuminated at grazing incidence by two intense light beams $f_1$ and $f_2$. The two beams $f_1$ and $f_2$ are from a single light source $S_O$ of the halogen lamp type. A set of appropriately oriented mirrors $M_1$ through $M_3$ and of focusing lenses $L_1$–$L_2$ and $L_3$–$L_4$ splits the main beam f emitted by the single source $S_O$ into two sub-beams $f_1$ and $f_2$ and directs them onto the telltale plate $P_{la}$ at grazing incidence in two mutually orthogonal directions.

The particles deposited on the telltale plate $P_{la}$ diffuse the incident light in all directions. A cadmium sulfide photoelectric cell $P_{HO}$ measures the light diffused in a direction orthogonal to the surface of the telltale plate $P_{la}$, i.e. at a diffusion angle of 90°. The luminous intensity causes its internal resistance to vary.

To be able also to observe the light diffused along the measuring axis by means of a microscope $M_i$, a mirror $M_{MO}$ is provided that is rotatable about an axis parallel to the surface of the telltale plate $P_{la}$. An appropriate mechanism $M_e$ drives the mirror $M_{MO}$. The mirror $M_{MO}$ is raised (position I) to enable observation by means of the microscope $M_i$ or at an angle of 45° (position II) to the surface of the telltale plate $P_{la}$ and to the diffused beam $L_{us}$ to deflect the beam $L_{us}$ 90° towards the photo-electric cell $P_{HO}$. The output signals are transmitted to electronic circuits $A_{MP}$ which include a measuring amplifier and circuits controlling the light source $S_O$.

The amplitude of the electrical signals at the output of the measurement amplifier is transmitted to measuring apparatus. They are representative of the quantity of particles deposited per unit surface area on the surface of the telltale plate $P_{la}$. Knowing the surface area and the time of exposure of the latter, it is possible to deduce the degree of contamination of the objects near which it was placed. If a number of plates are used an average can be calculated to enhance the accuracy of the measurement.

The apparatus described has three measurement ranges, the measurement amplifier $A_{MP}$ being provided with electronic circuits for switching between them automatically. The amplifier is fed with a stabilized voltage so that the measurements are nor sensitive to the variations in the mains power supply or to temperature variations. The luminous flux from the halogen lamp $S_O$ is stabilized by means of an additional photodiode (not shown) in a feedback circuit.

A calibration circuit (not shown) is also necessary. A potentiometer (not shown) is used to adjust the measurements in the calibration phase.

The above type of measuring apparatus represented a real step forward compared to previously known measurement methods. Nevertheless, it is not completely free of drawbacks. The latter can be summarized as follows:

- the usable measuring area is small: it is substantially limited to a 15 mm circle;
- aligning the incident light is difficult, in particular if the apparatus has been moved: these alignment problems are associated with the fixing of the halogen lamp and the four mirrors;
- the use of a white light source restricts the measurement to non-fluorescent particles;
- the optical background is typically limited to approximately 10 ppm on uncontaminated plates due to problems of stray light.

SUMMARY OF THE INVENTION

The invention has the aim of alleviating the disadvantages of the prior art device just described, some of which have just been summarized, whilst preserving its advantages.

To this end, in accordance with an important feature of the invention, the halogen lamp is replaced with a ring of light sources consisting of light-emitting diodes illuminating the surface of the telltale plate at grazing incidence in more than two different directions. In a preferred variant of the invention there are twelve light-emitting diodes equi-angularly distributed around a circle.

The invention therefore consists in apparatus for measuring fallout of particles on a surface of the type using a telltale plate of particular dimensions exposed for a particular time period to said fallout of particles, comprising means for illuminating said telltale plate when it is inserted into the measuring apparatus, opto-electronic means for detecting light diffused by said particles illuminated by said illumination means in a direction orthogonal to the surface of said telltale plate so as to measure the intensity of the light diffused in said orthogonal direction and to deduce therefrom the degree of contamination per unit surface of the telltale plate by said particles, characterized in that it includes a lower annular structure around said telltale plate and supporting an optical enclosure and in that said telltale plate illuminating means comprise at least two monochromatic optical sources fixed to the annular structure and arranged in space to illuminate the upper surface of the telltale plate in the same number of separate directions and at grazing incidence.

The structure of the measuring apparatus of the invention has many advantages, including:

The usable measuring area can be increased, typically from a 15 mm diameter circle to a 30 mm diameter circle, using a telltale plate with the same dimensions. This represents an enhancement factor of four, which is very important for statistical interpretation.

It is no longer necessary to use mirrors because the annular structure of light-emitting diodes can be fixed directly to an annular frame around the telltale plate. The angle of incidence is fixed. It is then possible to determine once and for all an optimized structure to obtain a maximum of diffused light for the aforementioned area and the lowest possible acquisition of stray light. This structure avoids re-adjustment of the optical paths (beams $f_1$ and $f_2$ in FIG. 1).

The light-emitting diodes generate monochromatic light, advantageously at a wavelength of 630 nm, which eliminates fluorescent effects when a 630 nm optical filter is placed in front of the electro-optic detector.

The optical enclosure is painted black enabling optical acquisitions typically less than or equal to 1 ppm (parts per million) (which must be compared with the typical value of 10 ppm previously referred to).

The structure of the apparatus in accordance with the invention authorizes very simple electronics associated with very low power consumption and consequently a very short warm up time. A very stable base is no longer necessary, because it is no longer necessary to adjust any mirrors, there being no mirrors, as previously indicated. Finally, because of the miniaturization that is possible, both mechanically and electronically, the apparatus has a much smaller overall size than the prior art apparatus shown in FIG. 1.

As described in detail below, the overall structure of the measuring apparatus comprises two main compartments: an optical enclosure and a detector part. As in the prior art, this arrangement authorizes either the use of a detector, in the case of the invention advantageously a CCD (Charge-Coupled Device) type detector, or the use of a microscope.

The complex internal calibration system is no longer necessary either. This eliminates further causes of errors in the measurements because of the complicated mechanism required to adjust the angle of deflection of the mirrors (reflecting the beams $f_1$ $f_2$) and a removable mirror ($M_{MO}$)

The invention will be better understood and other features and advantages will emerge from a reading of the following description with reference to the appended drawings, in which:

BRIEF DESCRIPTION OF THE DRAWINGS

FIG. 1 is a diagram illustrating one example of prior art apparatus for measuring fallout of particles on a surface using a telltale plate;

FIG. 2 is a diagram illustrating one example of apparatus in accordance with the invention for measuring fallout of particles on a surface using a telltale plate.

DESCRIPTION OF THE PREFERRED EMBODIMENTS

The measuring apparatus in accordance with the invention will now be described with reference to FIG. 2, which shows a preferred embodiment of such apparatus. The measuring method in itself does not differ from the measuring method used in the prior art and described already. There is therefore no utility in describing it again in detail. The telltale plate $P_{la}$ is exposed for a particular time period to the fallout of particles. The contamination is then measured by measuring the light diffused by the particles when the plate $P_{la}$ is illuminated by a plurality of beams at grazing incidence.

The apparatus 1 essentially comprises two parts:

a lower part including an annular structure 11 supporting light-emitting diodes $D_1$ and $D_x$ and an optical enclosure 10 disposed on top of the structure 11; and an advantageously annular upper part 12 adapted to support opto-electronic detector units 122.

The lower structure 11 includes a bottom opening 110 through which the telltale plate $P_{la}$ can be inserted. The telltale plate is inserted in a similar manner to that used for the device that is the subject matter of the previously mentioned British patent application. The light-emitting diodes, of which there are twelve in a preferred embodiment of the invention, are regularly distributed around the telltale plate $P_{la}$ to be lit. The light beams, for example $f_1$ and $f_x$, produced by the light emitting diodes $D_1$ and $D_x$ illuminate the telltale plate $P_{la}$ at a very low angle of incidence α, that is to say at grazing incidence. The angle α is typically in the order of 4°.

The number of light-emitting diodes, i.e. of light sources, is advantageously high, greater than two and preferably equal to twelve, as already mentioned. The subscript "$_x$" associated with $D_x$ is an arbitrary number dependent on the total number of light-emitting diodes. Conventional circuits 13 supply electrical power to the light-emitting diodes $D_1$–$D_x$.

The optical enclosure 10 has an axis of symmetry $\Delta_O$ and is fixed permanently to the annular base 11.

The upper part 12 disposed on the optical enclosure 10 supports, in addition to the previously mention opto-electronic detector units 122, an optical filter 121 disposed under the detector 122 and, in its lower part, a focusing lens 120. In the example shown in FIG. 2 the lens 120 is located where the annular structure 12 joins the optical enclosure 10.

The filter 121 is a narrow-band band-pass type filter. As already indicated, the light-emitting diodes, for example the diodes $D_1$ and $D_x$, emit substantially monochromatic light with a center wavelength of 630 nm. The pass-band of the filter 121 is centered on the same wavelength.

Removable fixing means 123 for the detector 122—filter 121 assembly are provided, for example of the conventional type using screws and leaf springs bearing on the aforementioned assembly to hold it in a housing 124 in the upper part of the structure 12.

The interior of the optical enclosure 10 is advantageously painted matt black to avoid unwanted reflections.

The opto-electronic detector units 122 are advantageously CCD type circuits, as already indicated. The electrical signal produced by conversion of the measured flux at an angle of incidence equal to 90° (along the axis of symmetry $\Delta_O$) of the light diffused by the particles contaminating the surface of the telltale plate $P_{la}$ are transmitted to electronic detector circuits 14. The latter include conventional amplifier circuits (not shown). The amplified signals are, as previously (FIG. 1), representative of the number of particles deposited per unit surface area and thereby of the degree of contamination. However, because of the specific features of the invention, the useable measuring area is typically a 30 mm diameter circle, for the same dimensions of the telltale plate $P_{la}$, representing enlargement by a factor of four.

The amplified signals can be used as such and transmitted to analog measuring apparatus or first be subject to analog-to-digital conversion, also in the conventional way, for exploitation by digital measuring apparatus, or even for processing and/or storage in signal processing circuits, for example a microcomputer.

As previously indicated, the apparatus of the invention is compatible with the use of a microscope. It is sufficient to demount the detector unit 122 and the associated filter 124 using the screw fixing means 123. The base of the microscope (not shown) must naturally be designed to enable it to be inserted into the compartment 124 and fixed by means of the previously mentioned screw fixing means 123.

There is no longer any requirement for a complicated calibration system. Simple protocols can be used. They consist, for example, in the quantified deposition of standardized polystyrene spheres with a diameter substantially equal to 40 $\mu$m onto a telltale plate $P_{la}$. Metal particles in a molten glass substrate can also be used.

A reading of the above description clearly indicates that the invention achieves the stated objectives and has the advantages summarized in the preamble to this description.

In particular, the apparatus of the invention does not include any removable or adjustable parts, at least within the optical enclosure, including the light-emitting diode support. The light-emitting diodes are fixed permanently and their large number achieves uniform illumination and maximal diffusion without requiring high power. The optical paths are not critical and do not require any adjustment in situ.

The structure overall is therefore much less complex and the apparatus can be miniaturized.

Fluorescent effects are minimized, which widens the field of particle types that can be measured.

It must nevertheless be clear that the invention is not limited to the embodiments described in detail, in particular with reference to FIG. 2.

In particular, as already indicated, the number of light-emitting diodes is not limited to twelve, although this number assures good illumination and high diffusion of light. Finally, light-emitting diodes having a wavelength of 630 nm are particularly suitable but they can be replaced by other types of monochromatic light source, for example laser diodes, although the latter are more costly.

If there is no need to use a microscope the CCD detector and filter assembly can be fixed permanently to the upper support, making the measuring apparatus of the invention more robust.

What is claimed is:

1. Apparatus (1) for measuring fallout of particles on a surface of the type using a telltale plate ($P_{la}$) of particular dimensions the upper surface of which is exposed for a particular time period to said fallout of particles, said apparatus comprising means for illuminating said telltale plate ($P_{la}$) when it is inserted into the measuring apparatus (1), said illuminating means being adapted to emit at least one light beam substantially parallel to said upper surface, opto-electronic means for detecting light diffused by said particles illuminated by said illumination means adapted to measure the intensity of the light diffused in a direction ($\Delta_O$) orthogonal to said surface and to deduce therefrom the degree of contamination per unit surface of the telltale plate ($P_{la}$) by said particles, characterized in that it includes a lower annular structure (11) around said telltale plate ($P_{la}$) and supporting an optical enclosure (10) and in that said telltale plate illuminating means comprise at least two monochromatic optical sources ($D_1$, $D_x$) fixed to the annular structure (11) and regularly spaced around the telltale plate to illuminate the upper surface of the telltale plate in the same number of separate directions and at grazing incidence.

2. Apparatus according to claim 1 characterized in that said monochromatic sources are light-emitting diodes ($D_1$, $D_x$) the emission from which is centered on a wavelength of 630 nm.

3. Apparatus according to claim 2 characterized in that there are 12 light-emitting diodes ($D_1$, $D_x$) equi-angularly distributed around said annular structure (11).

4. Apparatus according to claim 1 characterized in that said angle of incidence is substantially equal to 4°.

5. Apparatus according to claim 1 characterized in that said optical enclosure (10) has a cylindrical structure with an axis of symmetry ($\Delta_O$) orthogonal to the surface of said telltale plate ($P_{la}$) and in that the inside walls of said enclosure are covered with matt black paint to prevent unwanted reflections.

6. Apparatus according to claim 5 characterized in that said enclosure is surmounted by an upper annular structure (12), in that said structure (12) supports said opto-electronic detector means and in that said opto-electronic detector means comprise charge-coupled semiconductor circuits (122).

7. Apparatus according to claim 6 characterized in that said upper annular structure (12) also supports an optical band-pass filter disposed under said opto-electronic detector means (122) and the center wavelength of which is matched to the emission wavelength of said monochromatic optical sources ($D_1$, $D_x$).

8. Apparatus according to claim 6 characterized in that said upper annular structure (12) additionally supports, in its lower part, an optical lens (120) for focusing the light diffused onto said opto-electronic detector means (122).

9. Apparatus according to claim 6 characterized in that said upper annular structure (12) is provided with means for removably fixing said opto-electronic detector means (122) and where applicable said filter (121) which can be removed in order to replace them with a microscope for direct observation of the telltale plate ($P_{la}$).

10. Apparatus according to claim 9 characterized in that said removable fixing means comprise screw and leaf spring type means (123) for retaining said opto-electronic detector means (122) and where applicable said filter (121) in a housing (124) in the upper part of said upper annular structure (12).

* * * * *